(12) United States Patent
Cobianu et al.

(10) Patent No.: US 10,663,425 B2
(45) Date of Patent: May 26, 2020

(54) FET AND FIBER BASED SENSOR

(71) Applicant: Honeywell International Inc., Morris Plains, NJ (US)

(72) Inventors: Cornel P. Cobianu, Bucharest (RO); Bogdan-Catalin Serban, Bucharest (RO); Viorel Georgel Dumitru, Prahova (RO); Octavian Buiu, Bucharest (RO); Alisa Stratulat, Bucharest (RO); Mihai Brezeanu, Bucharest (RO)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 16/236,139

(22) Filed: Dec. 28, 2018

(65) Prior Publication Data

US 2019/0154630 A1    May 23, 2019

Related U.S. Application Data

(63) Continuation of application No. 15/249,522, filed on Aug. 29, 2016, now Pat. No. 10,197,526.

(30) Foreign Application Priority Data

Sep. 3, 2015 (EP) .................................... 15183782

(51) Int. Cl.
*G01N 27/414* (2006.01)
*H01L 29/06* (2006.01)
(Continued)

(52) U.S. Cl.
CPC ..... *G01N 27/4141* (2013.01); *G01N 27/4146* (2013.01); *G01N 33/0047* (2013.01);
(Continued)

(58) Field of Classification Search
CPC ........ G01N 27/04; G01N 27/02; G01N 27/06; G01N 33/18; G01N 27/045
(Continued)

(56) References Cited

U.S. PATENT DOCUMENTS 4,072,200 A * 2/1978 Morris ...................... E21B 7/04
175/45
4,933,640 A * 6/1990 Kuckes ............. E21B 47/02216
166/66.5
(Continued)

FOREIGN PATENT DOCUMENTS

WO    WO-2014060954 A1    4/2014

OTHER PUBLICATIONS

"U.S. Appl. No. 15/249,522, Advisory Action dated Aug. 9, 2018", 3 pgs.
(Continued)

*Primary Examiner* — Giovanni Astacio-Oquendo
(74) *Attorney, Agent, or Firm* — Schwegman Lundberg & Woessner, P.A.

(57) ABSTRACT

A gas sensor includes a field effect transistor supported on an oxide layer of a substrate, the field effect transistor having a doped source ($p^+$ doped for T-FET and n+ doped for FET) and an n+ doped drain separated by an channel region (intrinsic for T-FET or slightly p-doped for FET), and a floating gate separated from the channel region by a gate oxide, a passivation layer covering the floating gate, and a sensing layer supported by the passivation layer, the sensing layer comprising nanofibers.

20 Claims, 5 Drawing Sheets

(51) Int. Cl.
*H01L 29/788* (2006.01)
*H01L 29/78* (2006.01)
*H01L 29/66* (2006.01)
*H03F 3/45* (2006.01)
*G01N 33/00* (2006.01)

(52) U.S. Cl.
CPC .... *H01L 29/0649* (2013.01); *H01L 29/6697* (2013.01); *H01L 29/788* (2013.01); *H01L 29/7832* (2013.01); *H03F 3/45179* (2013.01); *G01N 27/4148* (2013.01); *H03F 2200/261* (2013.01)

(58) Field of Classification Search
USPC .................................. 324/693, 600, 649, 691
See application file for complete search history.

(56) References Cited

U.S. PATENT DOCUMENTS

| | | | |
|---|---|---|---|
| 5,039,981 | A | 8/1991 | Rodriguez |
| 6,617,972 | B2 | 9/2003 | Takarada et al. |
| 7,408,461 | B2 | 8/2008 | Fluck |
| 8,779,729 | B2 | 7/2014 | Shiraishi |
| 2002/0062992 | A1* | 5/2002 | Fredericks ............. E21B 47/00 175/40 |
| 2005/0242817 | A1 | 11/2005 | Hoult |
| 2007/0000778 | A1 | 1/2007 | Hsiung et al. |
| 2008/0062022 | A1* | 3/2008 | Melanson ............. H03M 3/464 341/143 |
| 2008/0079444 | A1* | 4/2008 | Denison ................ G01D 5/24 324/679 |
| 2009/0204350 | A1* | 8/2009 | Govil ................. B81C 99/0045 702/65 |
| 2012/0098518 | A1 | 4/2012 | Unagami et al. |
| 2014/0131774 | A1 | 5/2014 | Lee et al. |
| 2017/0067849 | A1 | 3/2017 | Cobianu et al. |

OTHER PUBLICATIONS

"U.S. Appl. No. 15/249,522, Final Office Action dated Jun. 20, 2018", 6 pgs.
"U.S. Appl. No. 15/249,522, Non Final Office Action dated Nov. 8, 2017", 8 pgs.
"U.S. Appl. No. 15/249,522, Notice of Allowance dated Sep. 24, 2018", 9 pgs.
"U.S. Appl. No. 151249,522, Response filed Jan. 18, 2018 to Non Final Office Action dated Nov. 8, 2017", 7 pgs.
"U.S. Appl. No. 15/249,522, Response filed Jul. 26, 2018 to Final Office Action dated Jun. 20, 2018", 7 pgs.
"U.S. Appl. No. 15/249,522, Response filed Sep. 6, 2018 to Advisory Action dated Aug. 9, 2018", 6 pgs.
"European Application Serial No. 15183782.0, Extended European Search Report dated Dec. 16, 2015", 11 pgs.
Arena, A, et al., "Flexible ethanol sensors on glossy paper substrates operating at room temperature", Sensors and Actuators B, 145(1), (2010), 488-494.
Khorami, Hamed Akbari, et al., "Ammonia sensing properties of ($SnO_2$—ZnO)/polypyrrole coaxial nanocables", Journal of Materials Science, 49(2), (2013), 685-690.
Sarkar, Deblina, et al., "Tunnel-field-effect-transistor based gas-sensor: Introducing gas detection with a quantum-mechanical transducer", Applied Physics Letters, 102(2), 023110, (2013), 5 pgs.
Zhan, Shuang, et al., "A Novel Flexible Room Temperature Ethanol Gas Sensor Based on $SnO_2$ Doped Poly-Diallyldimethylammonium Chloride", Sensors, 13(4), (2013), 4378-4389.

* cited by examiner

FET AND FIBER BASED SENSOR

CROSS REFERENCE TO RELATED APPLICATIONS

The present application is a continuation of and claims the benefit of priority to U.S. application Ser. No. 15/249,522, filed Aug. 29, 2016, which application claims priority to European Patent Application No. 15183782.0, filed Sep. 3, 2015, which applications are incorporated herein by reference in their entirety.

BACKGROUND

The continuous improvement of the performance and miniaturization of the sensors followed by their increased connectivity have triggered the development of the Internet of Things (IoT) for consumer applications. It is now the time for industrial IoT, where intelligent components will be used for connecting manufacturing lines, homes, hospitals, buildings, airports and workers to the Internet and thus, a real time (management) decision/can be obtained by analyzing big volumes of data provided by sensors and sensor networks. Connected workers working in a harsh environment (i.e. toxic and flammable gases ambient) may benefit from networked toxic gas sensors. However, current gas sensors consume significant amounts of power, making it difficult to be integrated in such a network.

Current gas sensors for toxic and flammable gases based on metal oxides, employing either calorimetric or chemoresistive detection principles, require high electric power consumption levels (100-200 mW), making them unsuitable for networked operation. Microelectromechanical systems (MEMS)-based gas sensors are currently emerging as commercial products with lower power consumption levels envisaged for their operation. However, even the announced minimum power consumption level for these structures (15 mW when operated in pulse width modulation) is still high enough to prevent their integration in wide, IoT-connected networks.

SUMMARY

A gas sensor includes a field effect transistor supported on an oxide layer of a substrate, the field effect transistor having a doped source ($p^+$ for a tunnel FET and n+ for a FET) and an $n^+$ doped drain separated by an intrinsic channel region, and a floating gate separated from the intrinsic channel region by a gate oxide, a passivation layer covering the floating gate, and a sensing layer supported by the passivation layer, with the sensing layer comprising nanofibers.

A circuit includes a gas sensor including a field effect transistor supported on an oxide layer of a substrate, the field effect transistor having a doped source and an $n^+$ doped drain separated by an intrinsic channel region, and a floating gate separated from the intrinsic channel region by a gate oxide, a passivation layer covering the floating gate, and a sensing layer supported by the passivation layer, the sensing layer comprising nanofibers. A reference gas sensor includes a field effect transistor supported on an oxide layer of a substrate, the field effect transistor having a doped source and an $n^+$ doped drain separated by an intrinsic channel region, and a floating gate separated from the intrinsic channel region by a gate oxide, a passivation layer covering the floating gate, a sensing layer supported by the passivation layer, the sensing layer comprising nanofibers, and a blocking layer disposed over the sensing layer to block gas from reaching the sensing layer. A differential amplifier is coupled to respective drains of the gas sensor and reference gas sensor to provide an output voltage representative of a gas to be sensed.

A method includes exposing a nanofiber sensing layer of a field effect transistor based gas sensor to a gas that changes a capacitance and work function of the sensing layer and hence current through a channel of the field effect transistor, obtaining a drain voltage of a reference sensor having the same construction as the gas sensor with the addition of a blocking layer blocking the gas from the nanofiber sensing layer of the reference sensor, and amplifying a difference in drain voltages of the gas sensor and reference sensor to obtain an output signal representative of exposure of the nanofiber sensing layer to the gas.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Figure 1:
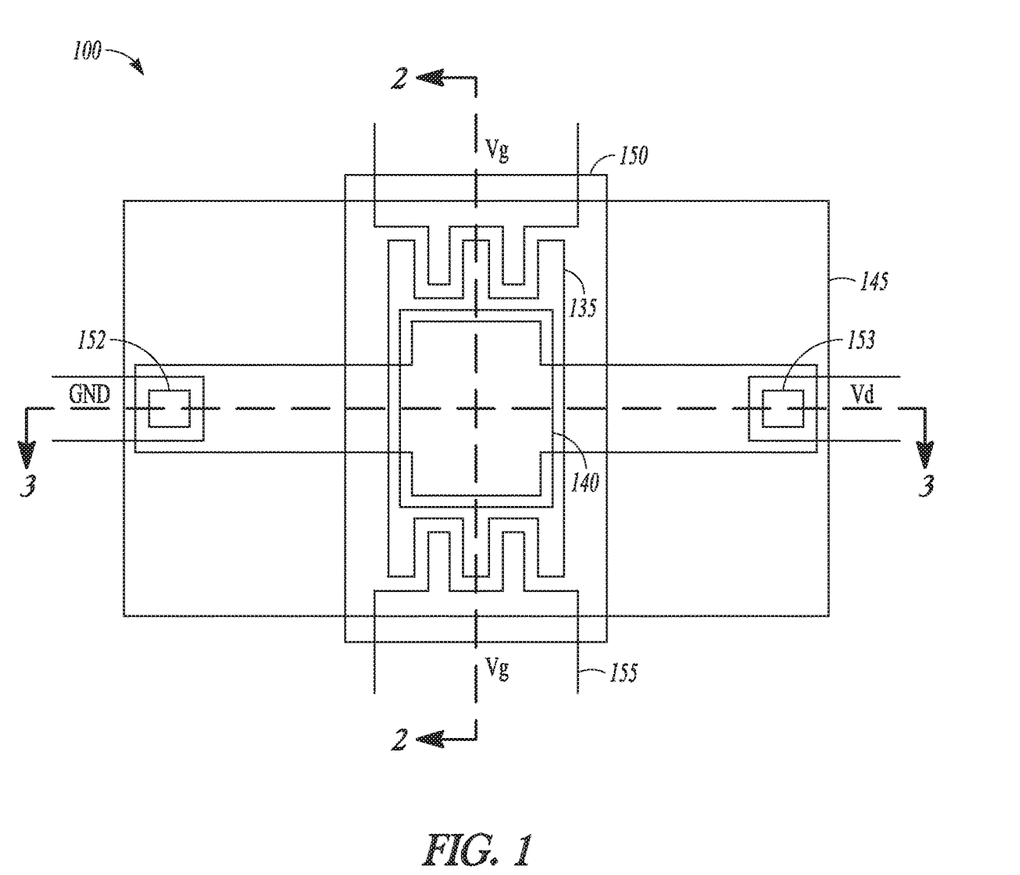
FIG. 1 is a top view of a horizontal capacitive coupled floating gate sensor according to an example embodiment.
Figure 2:
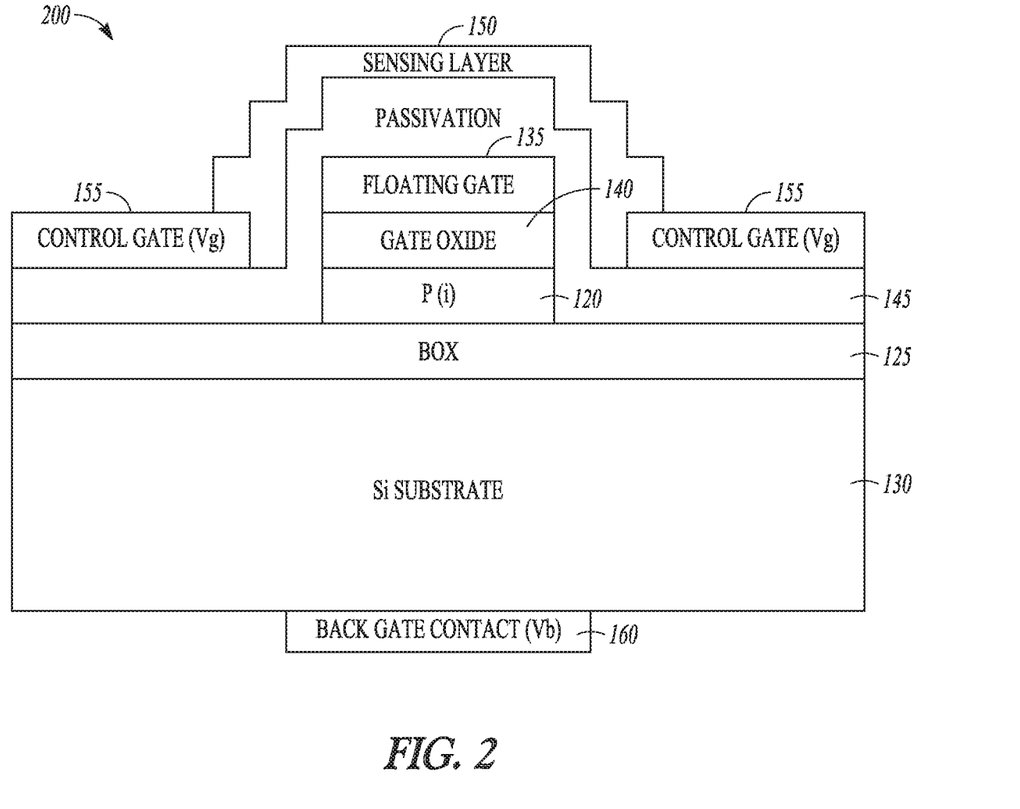
FIG. 2 is a cross section view of the sensor of FIG. 1 taken along lines 2-2.
Figure 3:
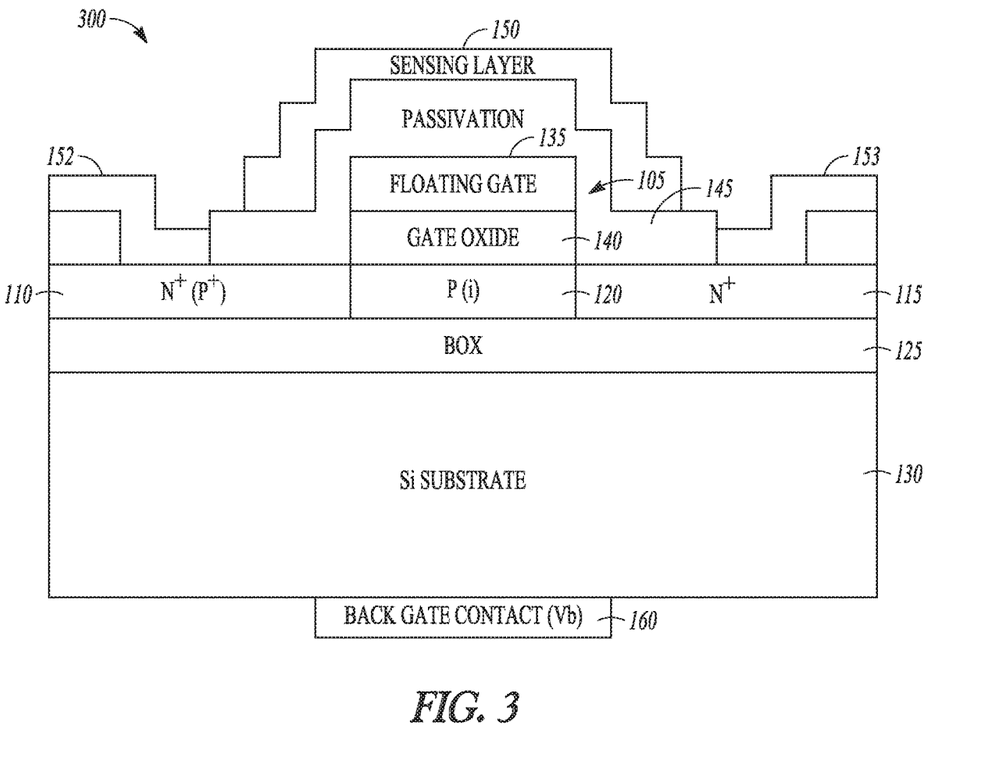
FIG. 3 is a cross section view of the sensor of FIG. 1 taken along lines 3-3.

A sensor for room temperature detection of ethanol ($C_2H_5OH$) vapors utilizes a high sensitivity field effect transistor (FET) (like Tunnel-FET or Fully Depleted Silicon On Insulator (FD-SOI) FET) and nanostructured inorganic-organic nanofibers, prepared by means of a combined sono-chemistry-electrospinning method. FD-SOI monolithic technology may be used for the realization of a FET-based $C_2H_5OH$ sensor at room temperature. The T-FET device operating in the subthreshold regime may have a subthreshold swing (SS) of about 15-20 mV/decade of current, which is much lower than the value of 60 mV/decade of classical transistors. This small SS value results in a high detection sensitivity. FIG. 1 is a top view of a monolithically formed gas sensor 100 utilizing a high sensitivity field effect transistor (FET) in combination with a nanofiber sensing portion. FIG. 2 is a cross section view of the sensor of FIG. 1 taken along lines 2-2. FIG. 3 is a cross section view of the sensor of FIG. 1 taken along lines 3-3. The numbering of elements in FIGS. 1, 2, and 3 is consistent.

Gas sensor 100 in one embodiment utilizes a fully depleted SOI tunneling FET (FD-SOI-T-FET) device 105 of $p^+$-i-$n^+$ type as shown in cross section in FIG. 3. In further embodiments, a fully depleted silicon on insulator FET (FD-SOI FET) of type $n^+$-p-$n^+$ type as shown also at 105 in FIG. 3 may be used. The FD-SOI-T-FET device has a $p^+$-doped source 110 separated from an $n^+$-doped drain 115 by an intrinsic region 120, which also serves as a "channel". The doping of the FD-SOI-T-FET device 105 is illustrated in parenthesis in FIG. 3 where different from the FD-SOI-FET.

The source 110, drain 115, and channel 120 are formed thin silicon film located on a buried oxide (BOX) layer 125 of a substrate 130. The substrate 130 may be silicon in one embodiment. The Source 110 is $p^+$ doped for FD-SOI-T-FET and $n^+$ doped for FD-SOI-FET. The drain 115 may be N+ doped. The intrinsic region 120 may be undoped (for FD-SOI-T-FET) or lightly P doped (for FD-SOI-FET). A floating gate 135 is positioned above the intrinsic region 120 of FD-SOI-T-FET and above the p-type region of the FD-SOI-FET and separated from it by a gate oxide 140. A passivation layer 145 is formed over the floating gate 135, followed by a top nanofiber sensing layer 150. A source contact 152 and drain contact 153 are also illustrated, coupled directly to the respective source 110 and drain 115.

In a T-FET device, a gate bias may be applied so that electron accumulation occurs in the intrinsic region. At sufficient gate bias, band-to-band tunneling (BTBT) occurs when the conduction band of the intrinsic region aligns with the valence band of the source. Electrons from the valence band of the source tunnel into the conduction band of the intrinsic region and current can flow across the device. As the gate bias is reduced, the bands becomes misaligned and current can no longer flow. The sensing layer 150 plays a role in the level of the gate bias that is applied as described in further detail below.

FIGS. 1 and 2 illustrate a control gate 155 that is horizontally interdigitated with the floating gate 135 such that it is horizontally capacitive coupled (HCC) with the floating gate 135. A back gate contact ($V_b$) 160 is shown coupled to the substrate 130. FIG. 1 illustrates perimeters or boundaries of the various elements in a top view, with FIG. 2 illustrating the elements in a cross section.

As seen in FIG. 1, the control gate 155 is interdigitated with the floating gate 135 such that voltage applied on the control gate 155 is capacitively coupled in the horizontal direction to the floating gate 135 by means of capacitance of the sensing layer ($C_s$) and the capacitance of the passivation layer ($C_{Pass}$). These two capacitances form a capacitive voltage divider together with the capacitance of the oxide ($C_{ox}$) and the parasitic capacitance from the floating gate to the ground ($C_{par}$). The last two being connected in parallel to the ground. The source 110 is also considered ground. Note that the passivation layer 145 extends beneath the control gate at least in the area of interdigitization. The passivation layer 145 also extends under the sensing layer 150 and completely covers the floating gate 135 and gate oxide 140. The sensing layer 150 is formed over the passivation layer 145 and may contact the control gate 155, and may stop short of the source and drain contacts 152 and 153, which are formed though the passivation layer to contact the source 110 and drain 115 respectively.

A differential. FET based sensor for ethanol ($C_2H_5OH$) detection at room temperature operates by means of a combined effect of capacitance change of the organic-inorganic composite nanofibers and the work function change due to the ethanol gas reacting with the inorganic-organic composite sensing layer. Here, the organic part may be polydialyldimethylammonium chloride (PDDAC) and the inorganic part may be made of metal oxides like $SnO_2$, or Sb-doped $SnO_2$, or ITO (indium tinoxide).

Figure 4:
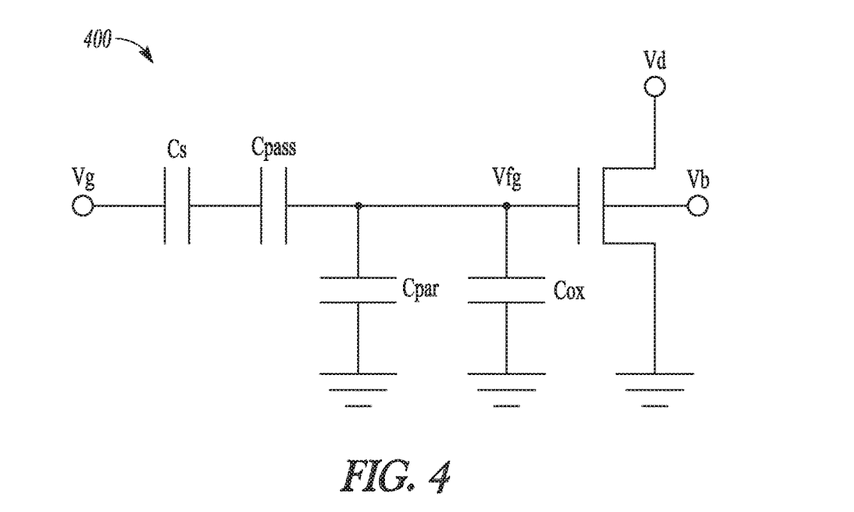
FIG. 4 is a circuit diagram of an equivalent electric circuit of the sensor of FIG. 1.

From the equivalent electric circuit shown in FIG. 4, one can easily calculate the voltage on the floating gate ($V_{fg}$) as follows:

$$V_{fg}=[C_e(C_e+C_{ox}+C_{par})]*[V_g+(\Delta\Phi/e)] \quad [1]$$

where $C_e=C_s*C_{pass}(C_s+C_{pass})$, and e is the electron charge and $\Delta\Phi$ is the variation of work function.

Given the notation $\beta=C_e(C_e+C_{ox}+C_{par})$, where $\beta$ is called the coupling factor of capacitive voltage divider, and $\beta<1$, then Equation [2] follows:

$$V_{fg}=\beta*[V_g+(\Delta\Phi/e)] \quad [2]$$

Equation [2] shows that if the control gate 155 potential ($V_g$) is equal to zero, the floating gate 135 potential is entirely provided by the change in the electron work function of sensing layer 150 due to the gas to be detected. The equation also shows that the capacitive voltage divider reduces the contribution of the work function change to the voltage on the floating gate 135. Finally, the change of the capacitance of the sensing layer ($C_s$) is also responsible for the value of the change in the drain current 115 through the FET sensor as a function of gas to be detected. For this reason, the equivalent capacitance of the sensing layer and passivation layer may be much higher than the capacitance of the gate oxide and parasitic capacitance of the floating gate to ground, providing a high sensitivity to $C_2H_5OH$. The interdigitated capacitive coupling between the control gate 155 and the floating gate 135 may be utilized in order to obtain a maximum value for the divider coupling factor, i.e. $\beta$ to converge to 1. This is shown in top view in FIG. 1. The number of digits, their length and width, the spacing between digits, as well as the thickness of the sensing layer and passivation layer may be all design variables, which will help to obtain a desired divider coupling factor, $\beta$.

The sensing model of the horizontal capacitive coupling floating gate fully depleted SOI Tunnel FET (or simple T-FET) HCC-FG-FD-SOI T-FET) for ethanol ($C_2H_5OH$) gas sensor 100 based on hybrid organic (PDDAC)-inorganic (ITO, $SnO_2$, $SnO_2$—Sb), can be explained as follows. PDDAC is a charged polyelectrolyte, which acts a binder to the substrate and to the ceramic nanoparticles, and, as a dopant to the metal oxides. In clean air, there is a certain electrostatic equilibrium between the positive charges of the organic polyelectrolyte (PDDAC) and negative charges of the surface of the metal oxide. The entire composite sensing layer shows a certain depletion capacitance, as result of this process.

In the presence of the ethanol, due to the oxidation reaction of the ethanol with the sensing layer and the associated charge transfer reactions, the depletion capacitance between the PDDAC and metal oxide will change and this change will be detected by the FET. On the other hand, the chemical composition of the interface between the floating gate and the sensing layer will be changed by the presence of ethanol, and this will bring a change in the work function of the sensing layer 150 surface at the interface with floating gate in ethanol ambient. In conclusion, at the level of the FET sensing, the ethanol detection at room temperature is based on both capacitance change and work function change of the sensing layer 150. When a gas to be detected is applied to the HCC-FG-FET sensor, the triple phase boundary region consisting of gas, control gate and ethanol sensing layer will determine a change of the sensing layer work function (WF). This change in the work function combined with the change in the sensing layer capacitance ($C_S$) will generate a change in threshold voltage and drain current of the sensing FET, which can be measured during sensor operation.

For a maximum response of the ethanol sensing layer at room temperature, a high specific surface area is targeted. This is obtained by sonochemistry followed by an electrospinning process, which by the nature of the electrospinning process will generate nanowires of the metal oxide embedded in PDDAC, which will be preserved after the thermal annealing.

As mentioned above, both sensing layer WF (affecting the threshold voltage of FET) and the capacitance of the MOX sensing layer will be changed as a function of the gas to be detected. The contribution of these two variations ($\Delta V_{th}$ and $\Delta C_s$) to the sensor response will be determining the sensor behavior.

As mentioned above, the gas sensor may be monolithically formed. The monolithic approach avoids the prior art complex hybrid technology, where an air gap was needed between the floating gate and a control gate that also contains the sensing layer. Such prior hybrid technologies had the added complexity of having to bond two chips to one to the other to obtain an air gap. In the present embodiments, an FD-SOI monolithic technology is utilized for the sensing (T) FET and a reference (T) FET 500 in FIG. 5 may be located on the same chip. The sensing and reference (T) FETs have outputs that are connected to an instrumentation amplifier 600 in FIG. 6, which will provide a voltage proportional to the $C_2H_5OH$ in the ambient, while the common mode signals originating from temperature variation, electronic noise, aging of the materials are all rejected with a high common mode rejection ratio (CMRR).

Figure 5:
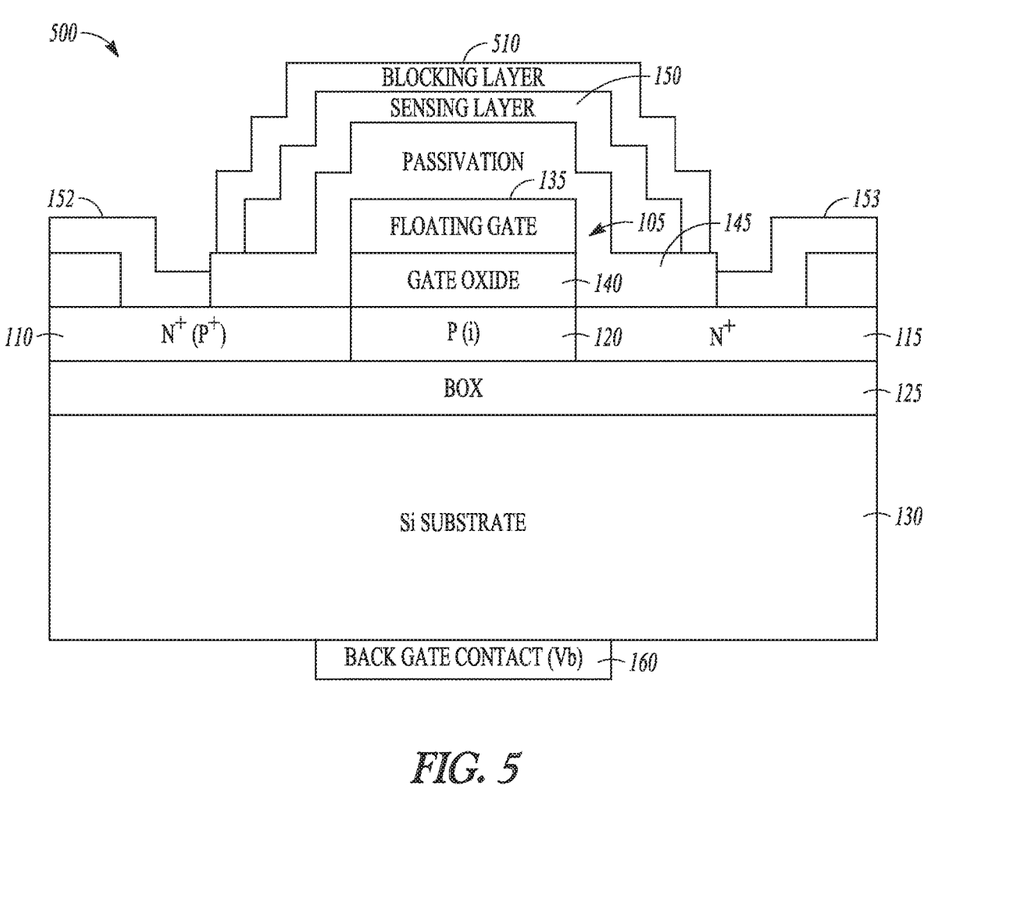
FIG. 5 is a cross section view of a reference sensor according to an example embodiment.

In order to obtain the reference FET 500, shown in cross section in FIG. 5, the same technology flow is used as in the case of sensing FET, but with the addition of covering the sensing layer with a blocking layer such as $SiO_2$ layer 510 which will block the $C_2H_5OH$ gas to reach the organic-inorganic sensing layer 150 from below. In one embodiment, the $SiO_2$ layer 510 extends laterally beyond the perimeters of the floating gate 135 and intrinsic region 120, and in further embodiments, may completely cover the sensing layer 150. Like layers are identified with the same references numbers as used in FIGS. 1-3. Other materials like plasma enhanced chemical vapor deposited (PECVD) silicon nitride ($Si_xN_y$), or silicon oxinitride ($SiO_xN_y$) may be used as the blocking layer in further embodiments.

In one embodiment, FD-SOI technology may be used for the fabrication of the HCC sensing FET and HCC reference FET (either in the configuration of T-FET or FET which will be used for the differential detection of the $C_2H_5OH$ by means of both gate capacitance and work function change as a function of ambient $C_2H_5OH$ change. The reference HCC FET is obtained by depositing a thick $SiO_2$ layer 510 of about 0.5-1 µm above the $C_2H_5OH$ sensing layer, so that no $C_2H_5OH$ gas is able reach the sensing film.

Both the sensing HCC FET and reference HCC FET have a control gate which is capacitively coupled to the floating gate. The electric potential of the control gate is transferred via a capacitive divider to a floating gate. The capacitive voltage divider consists of a series of capacitances of the sensing film, a passivation layer (like a $Si_3N_4$) and the parasitic capacitance of the floating gate (in parallel with the floating gate capacitance). In order to assure a good coupling coefficient of the work function change to the floating gate of the FET, a high capacitance of the sensing layer and passivation layer should be accompanied by a low parasitic capacitance of the floating gate. The interdigitated structure of the control gate electrode and floating gate electrode will contribute to the high value of the coupling coefficient, and it will be used as design parameter. In order to decrease the parasitic capacitance of the floating gate, the interdigitated electrode structure will be located above a buried oxide, BOX, specific of the SOI technology.

Figure 6:
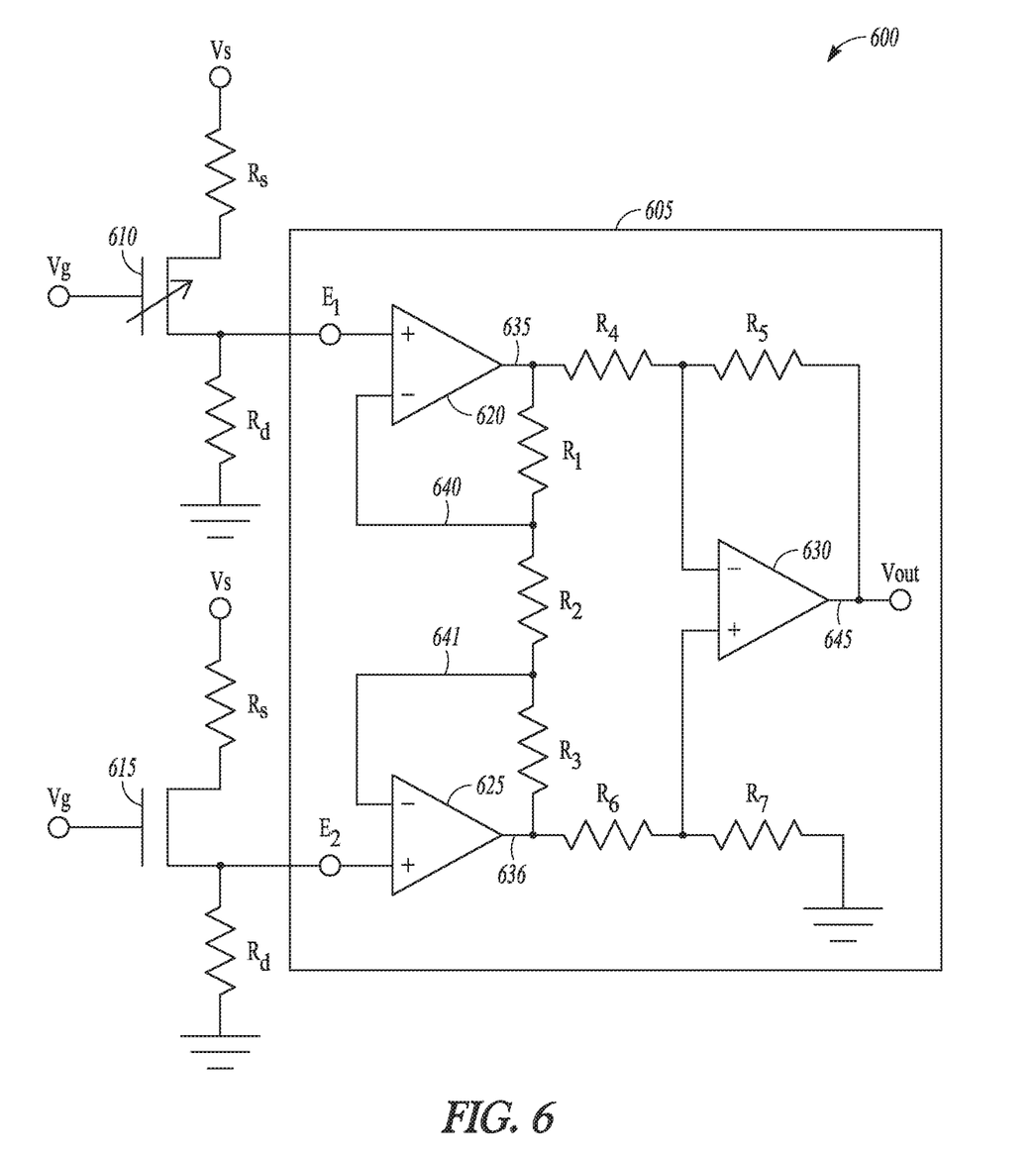
FIG. 6 is block schematic diagram of a differential signal processing circuit according to an example embodiment.

In the presence of the $C_2H_5OH$ gas, for the same gate voltage and source voltage applied to both reference and sensing FET, only the drain current and output voltage of the sensing FET will be changed. Therefore amplifying a difference in the output voltage from the sensing FET and reference FET provides a voltage signal which is proportional to the $C_2H_5OH$ signal the aging and temperature effects are cancelled. For an accurate reading of this voltage difference, an electronic signal amplifier 600 as shown in FIG. 6 may be used. A differential reading circuit for $C_2H_5OH$ detection is formed by connecting the outputs from the HCC sensing FET indicated at 610 and reference HCC FET indicated at 615 to an instrumentation amplifier made of three operational amplifiers 620, 625, and 630, and where, by proper design, the common mode rejection ratio (CMRR) is very high. Each of the FETs is illustrated with a source resistance $R_s$ and drain resistance Rd. Operational amplifiers 620 and 625 have positive inputs coupled to respective FET 610 and 615 drains. The negative inputs are coupled via resistors R1 and R3 that are coupled to respective outputs 635, 636 of the operational amplifiers 620 and 625 via feedback loops 640, 641. A resistor $R_2$ is coupled between $R_1$ and $R_3$. The outputs of operational amplifiers 635, 636 are coupled via respective resistors $R_4$ and $R_6$ to negative and positive inputs of operational amplifier 630. The output 645 of operational amplifier 630 is the output $V_{out}$ of the amplifier 600 and is coupled via resistor $R_5$ to its negative input, while the positive input of operational amplifier 630 it coupled to ground via resistor RT.

Values of resistances may be evaluated using the following relationships:

If:

$$R_5/R_4 = R_7/R_6 = k \text{ and}$$

$$2*R_1/R_2 = 2*R_3/R_2 = G$$

Then:

$$R_1 = R_3$$

Common mode Rejection Ratio (CMRR)=∞

(Common mode gain=0)

$$V_{out} = -k*(G+1)*(E_1-E_2) = A_d*(E_1-E_2)$$

Differential gain ($A_d$) can be changed from $R_2$ change, without affecting CMRR.

This differential approach ($V_{out} = A_d*(E_1-E_2)$) will minimize the sensor drift by subtracting the common mode signals coming from effects of temperature, polymer aging, and electronic noise.

The value of voltage $E_1$ will be different from $E_2$, due to the ethanol absorption and reaction with metal oxide of sensing HCC-FG-FET. The ethanol reaction to the sensing film will generate electrons which will be given back to the sensing film, and this will finally determine a change of the capacitance of sensing layer and its work function in the sensing HCC-FG FET transistor and thus one changes also the threshold voltage of the sensing FET, and finally, it will change the drain current. The ethanol will not enter the reference layer, so $E_2$ voltage value will follow only the changes due to common mode signals (temperature, ageing, noise).

In one embodiment, the instrumentation amplifier can be integrated on the same chip with the sensing and reference FET, or it can be used as it is from a commercial supplier, like Analog Devices.

In one embodiment, a method of making the nanostructured $C_2H_5OH$ layer or sensing layer 150 may be performed by putting together sonochemistry and electrospinning to obtain nanowires based sensing layer with a thickness in the range of 0.5-3 µm. Large surface area films based on nanowires of inorganic-organic composites may be directly deposited on the silicon chip by means of a shadow mask.

1. Selection of SOI wafer with a very thin silicon film (10-30 nm) on a very thin buried $SiO_2$ film (10-30 nm) on a bulk silicon substrate.
2. Photoresist deposition and patterning for defining the ion implantation regions of source and drain. For the case of n-type FDSOI FET transistor formation, the source and drain will be both n+ doped by arsenic implantation (single mask process). For the case of T-FET transistor, the source could be for example p+ doped (by boron imp-implantation), while the drain will be n+ doped by arsenic implantation. In the case of T-FET process, two masking processes may be used to obtain the source and drain region, one for each type of doping.
3. Gate oxide growth. The gate dielectric could be either $SiO_2$ thermally grown or the $HfO_2$ deposition by vapor chemical deposition, for example.
4. Floating gate deposition and patterning. It can be doped polysilicon obtained by chemical vapor deposition process.
5. Passivation layer deposition and patterning. This layer can be plasma enhanced chemically vapor deposited (PECVD) layer of $Si_3N_4$ or $SiO_2$.
6. Al metal deposition and patterning for performing source and drain contact.
7. Sensing layer deposition by direct electrospinning of the PDDAC-metal organic composite through a shadow mask. Nanofibers of PDDAC-metal organic composite will strongly adhere to the substrate due to PDDAC acting as a binder.

II. Process flow for the fabrication of the reference FET.

The sensing FET and the reference FET will be made on the same chip and with the same technological steps as described above.

The only difference will be that the sensing layer of the reference FET will be covered with a $SiO_2$ layer, so that ambient gas cannot reach the sensing layer.

For the differential sensor realization, the output of the two transistors will be connected to the instrumentation amplifier as described in FIG. 6.

III. Fully integrated differential HCC FD-SOI-FET sensor for $C_2H_5OH$ detection. In this case the, the instrumentation amplifier is also integrated on the same chip with the sensing and reference FET.

IV. Process flow for the preparation of the PDDAC-ITO sensing layer.

1. 2.5 grams of PDDAC and 1 gram of hydroxypropyl cellulose are dissolved in 25 ml of deionized water, at room temperature.
2. 2 grams of ITO nanopowder is dispersed in the PDDAC solution
3. The mixture from step 2 is exposed for 2 hours to low intensity ultrasonic irradiation in a sonochemical reactor, at room temperature.
4. The homogeneous solution from above is loaded in a plastic syringe of an electrospinning reactor.
5. The silicon wafer covered with the shadow mask is placed on a grounded collector, which is located at a distance of 4-10 cm far from the plastic syringe with a metal needle biased at high voltage (15-25) kV.
6. Remove the shadow mask and evaluate the sensing layer based on nanofibers of PDDAC and ITO.
7. Final thermal treatment at 40-50° C.

Similar processes may be used for forming different nanowire-based sensing layers. A process flow for PDDAC-$SnO_2$ nanowire-based sensing layer can be made similarly starting from PDDAC solution and $SnO_2$ nanopowder and following the same procedure as above.

A process flow for PDDAC-$SnO_2$—Sb nanowire-based sensing layer can be made similarly starting from PDDAC and Sb doped $SnO_2$ powder and following the same procedure as above.

Examples

1. A gas sensor comprising:
a field effect transistor supported on an oxide layer of a substrate, the field effect transistor having a doped source and an $n^+$ doped drain separated by a channel region, and a floating gate separated from the channel region by a gate oxide;
a passivation layer covering the floating gate; and
a sensing layer supported by the passivation layer, the sensing layer comprising nanofibers.

2. The gas sensor of example 1 and further comprising a control gate interdigitated with the floating gate.

3. The gas sensor of example 2 wherein the control gate is horizontally capacitively coupled to the floating gate.

4. The gas sensor of any of examples 2-3 and further comprising a back control gate contact coupled to the substrate.

5. The gas sensor of any of examples 1-4 wherein the nanofibers comprises an organic material and an inorganic material exhibiting both capacitance change and work function change responsive to exposure to $C_2H_5OH$.

6. The gas sensor of example 5 wherein the organic material comprises polydialyldimethylammonium chloride (PDDAC) and inorganic material comprises a metal oxide.

7. The gas sensor of example 6 wherein the metal oxide is $SnO_2$, Sb-doped $SnO_2$, or ITO (indium tinoxide).

8. The gas sensor of any of examples 1-7 wherein the sensing layer changes electron work function responsive to exposure to ethanol ($C_2H_5OH$).

9. The gas sensor of any of examples 1-8 and further comprising a blocking layer disposed over the sensing layer to block gas from reaching the sensing layer.

10. The gas sensor of any of examples 1-9 wherein the field effect transistor comprises a tunneling field effect transistor having an intrinsic channel and $p^+$ doped source.

11. The gas sensor of any of examples 1-9 wherein the field effect transistor comprises an $n^+$ doped source and a p doped channel.

12. A circuit comprising:
a gas sensor comprising:
a field effect transistor supported on an oxide layer of a substrate, the field effect transistor having a doped source and an $n^+$ doped drain separated by an channel region, and a floating gate separated from the channel region by a gate oxide;
a passivation layer covering the floating gate; and a sensing layer supported by the passivation layer, the sensing layer comprising nanofibers;
a reference gas sensor comprising:
a field effect transistor supported on an oxide layer of a substrate, the field effect transistor having a doped source and an n$^+$ doped drain separated by an channel region, and a floating gate separated from the channel region by a gate oxide;
a passivation layer covering the floating gate;
a sensing layer supported by the passivation layer, the sensing layer comprising nanofibers; and
a blocking layer disposed over the sensing layer to block gas from reaching the sensing layer; and
a differential amplifier coupled to respective drains of the gas sensor and reference gas sensor to provide an output voltage representative of a gas to be sensed.

13. The circuit of example 12 wherein the differential amplifier comprises:
a first operational amplifier coupled to the drain of the gas sensor;
a second operational amplifier coupled to the drain of the reference gas sensor; and
a third operational amplifier coupled to the outputs of the first and second operational amplifiers to provide the output voltage.

14. The circuit of example 13 wherein the first and second operational amplifiers comprises respective output feedback loops.

15. The circuit of any of examples 13-14 wherein the differential amplifier is operable to minimize gas sensor drift by subtracting common mode signals arising from temperature changes, polymer aging, and electronic noise.

16. The circuit of any of examples 12-15 wherein the nanofibers of the gas sensor and reference gas sensor comprise an organic material and an inorganic material exhibiting both capacitance change and work function change responsive to exposure to $C_2H_5OH$.

17. The circuit of any of examples 12-16 wherein the organic material comprises polydialyldimethylammonium chloride (PDDAC) and inorganic material comprises a metal oxide.

18. The circuit of example 17 wherein the metal oxide is $SnO_2$. Sb-doped $SnO_2$, or ITO (indium tinoxide).

19. A method comprising:
exposing a nanofiber sensing layer of a field effect transistor based gas sensor to a gas that changes a capacitance and work function of the sensing layer and hence current through a channel of the field effect transistor;
obtaining a drain voltage of a reference sensor having the same construction as the gas sensor with the addition of a blocking layer blocking the gas from the nanofiber sensing layer of the reference sensor; and
amplifying a difference in drain voltages of the gas sensor and reference sensor to obtain an output signal representative of exposure of the nanofiber sensing layer to the gas.

20. The method of example 19 wherein the difference in drain voltages is provided by a differential amplifier operable to minimize gas sensor drift by subtracting common mode signals arising from temperature changes, polymer aging, and electronic noise.

21. The method of any of examples 19-20 wherein the nanofibers comprise an organic material and an inorganic material exhibiting both capacitance change and work function change responsive to exposure to the gas comprising $C_2H_5OH$.

22. The gas method of example 21 wherein the organic material comprises polydialyldimethylammonium chloride (PDDAC) and inorganic material comprises $SnO_2$, Sb-doped $SnO_2$, or ITO (indium tinoxide).

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:
1. A method comprising:
exposing a nanofiber sensing layer of a field effect transistor-based gas sensor to a gas that changes a capacitance and work function of the sensing layer and hence current through a channel of the field effect transistor;
obtaining a drain voltage of a reference sensor having the same construction as the gas sensor with the addition of a blocking layer blocking the gas from the nanofiber sensing layer of the reference sensor; and
amplifying a difference in drain voltages of the gas sensor and reference sensor to obtain an output signal representative of exposure of the nanofiber sensing layer to the gas.

2. The method of claim 1 wherein the difference in drain voltages is provided by a differential amplifier.

3. The method of claim 1 wherein the nanofibers comprise an organic material and an inorganic material exhibiting both capacitance change and work function change responsive to exposure to the gas comprising $C_2H_5OH$.

4. The method of claim 3 wherein the organic material comprises polydialyldimethylammonium chloride (PDDAC) and inorganic material comprises $SnO_2$, Sb-doped $SnO_2$, or ITO (indium tinoxide) that has been irradiated in a sonochemical reactor.

5. The method of claim 1 wherein the field effect transistor comprises a tunneling field effect transistor having an intrinsic channel and p$^+$ doped source.

6. The method of claim 1 wherein the field effect transistor comprises an n$^+$ doped source and a p doped channel.

7. The method of claim 1 wherein the field effect transistor has a doped source and an n$^+$ doped drain separated by a channel region, and a floating gate separated from the channel region by a gate oxide.

8. The method of claim 7 wherein the field effect transistor has a control gate interdigitated with the floating gate.

9. The method of claim 8 wherein the control gate is horizontally capacitively coupled to the floating gate.

10. A method comprising:
exposing a first nanofiber sensing layer of a field effect transistor-based gas sensor to a gas that changes a capacitance and work function of the sensing layer and hence current through a channel of the field effect transistor;
obtaining a first drain voltage of the gas sensor;
preventing exposure of a second nanofiber sensing layer of a field effect transistor-based reference sensor to the gas, wherein the reference sensor has a same construction as the gas sensor with the addition of a block layer blocking the gas from the second nanofiber sensing layer of the reference sensor;
obtaining a second drain voltage of the reference sensor; and amplifying a difference in drain voltages of the gas sensor and reference sensor to obtain an output signal representative of exposure of the nanofiber sensing layer to the gas.

11. The method of claim 10 wherein the difference in drain voltages is provided by a differential amplifier operable to minimize gas sensor drift by subtracting common mode signals arising from temperature changes, polymer aging, and electronic noise.

12. The method of claim 10 wherein the nanofibers comprise an organic material and an inorganic material exhibiting both capacitance change and work function change responsive to exposure to the gas comprising $C_2H_5OH$.

13. The method of claim 12 wherein the organic material comprises polydialyldimethylammonium chloride (PD-DAC) and inorganic material comprises $SnO_2$, Sb-doped $SnO_2$, or ITO (indium tinoxide) that has been irradiated in a sonochemical reactor.

14. The method of claim 10 wherein the field effect transistor comprises a tunneling field effect transistor having an intrinsic channel and $p^+$ doped source.

15. The method of claim 10 wherein the field effect transistor comprises an $n^+$ doped source and a p doped channel.

16. A method comprising:
exposing a nanofiber sensing layer of a field effect transistor-based gas sensor, wherein the field effect transistor is supported on an oxide layer of a substrate, the field effect transistor having a doped source and an $n^+$ doped drain separated by an intrinsic channel region, and a floating gate separated from the channel region by a gate oxide, a passivation layer covering the floating gate, to a gas that changes a capacitance and work function of the sensing layer and hence current through a channel of the field effect transistor;
applying a gate bias such that electron accumulation occurs in the intrinsic channel region and current flows across the channel; and
detecting a change in the capacitance and work function based on the gas reacting with the sensing layer.

17. The method of claim 16 wherein the nanofibers comprise an organic material and an inorganic material exhibiting both capacitance change and work function change responsive to exposure to the gas comprising ethanol ($C_2H_5OH$).

18. The method of claim 17 wherein the organic material comprises polydialyldimethylammonium chloride (PD-DAC) and inorganic material comprises $SnO_2$, Sb-doped $SnO_2$, or ITO (indium tinoxide) that has been irradiated in a sonochemical reactor.

19. The method of claim 17 wherein exposing the sensing layer to the ethanol generates electrons to change the capacitance of the sensing layer and the work function to change a threshold voltage and drain current.

20. The method of claim 16 wherein the field effect transistor-based gas sensor includes a control gate interdigitated with the bias gate such that voltage applied on the control gate is capacitively coupled in a horizontal direction to the floating gate.

* * * * *